United States Patent
Privitera

(10) Patent No.: US 8,333,961 B2
(45) Date of Patent: Dec. 18, 2012

(54) NATURAL LINIMENT FOR TREATMENT OF SKIN CANCERS

(76) Inventor: James R. Privitera, Covina, CA (US)

(*) Notice: Subject to any disclaimer, the term of this patent is extended or adjusted under 35 U.S.C. 154(b) by 816 days.

(21) Appl. No.: 11/773,034

(22) Filed: Jul. 3, 2007

(65) Prior Publication Data

US 2009/0010913 A1    Jan. 8, 2009

(51) Int. Cl.
*A61K 38/54* (2006.01)
*A61K 38/43* (2006.01)
*A61K 38/00* (2006.01)
*A61K 31/00* (2006.01)
*A61P 35/00* (2006.01)

(52) U.S. Cl. ............ 424/94.21; 424/94.1; 424/94.2; 514/19.3; 514/19.2; 514/1.1; 514/1

(58) Field of Classification Search ............ 424/94.21
See application file for complete search history.

(56) References Cited

U.S. PATENT DOCUMENTS

| | | | |
|---|---|---|---|
| 4,515,779 A | 5/1985 | Elliott | |
| 4,725,438 A | 2/1988 | Leazer | |
| 4,955,857 A | 9/1990 | Shettigar | |
| 6,521,271 B1 * | 2/2003 | Phan | 424/756 |
| 7,195,781 B2 | 3/2007 | Miketin | |
| 2005/0260181 A1 * | 11/2005 | Girsh | 424/93.45 |

OTHER PUBLICATIONS

University of Maryland Medical Center, 2011, UMMC, accessed online at [http://www.umm.edu/altmed/articles/skin-cancer-000029.htm], accessed on Dec. 5, 2011, pp. 1-9.*

* cited by examiner

*Primary Examiner* — Ruth Davis
*Assistant Examiner* — Sheridan MacAuley
(74) *Attorney, Agent, or Firm* — Sanford Astor; Brooks Kushman P.C.

(57) ABSTRACT

A liniment composition for reversing or retarding the growth of cancerous skin tumors comprising primarily, pancreatin, pepsin, betaine HCL, emulsified vitamin A, and zinc, pancrelipase, fenugreek, papain, amylase and ox bile extract, with optional trace amounts of other ingredients.

11 Claims, 1 Drawing Sheet

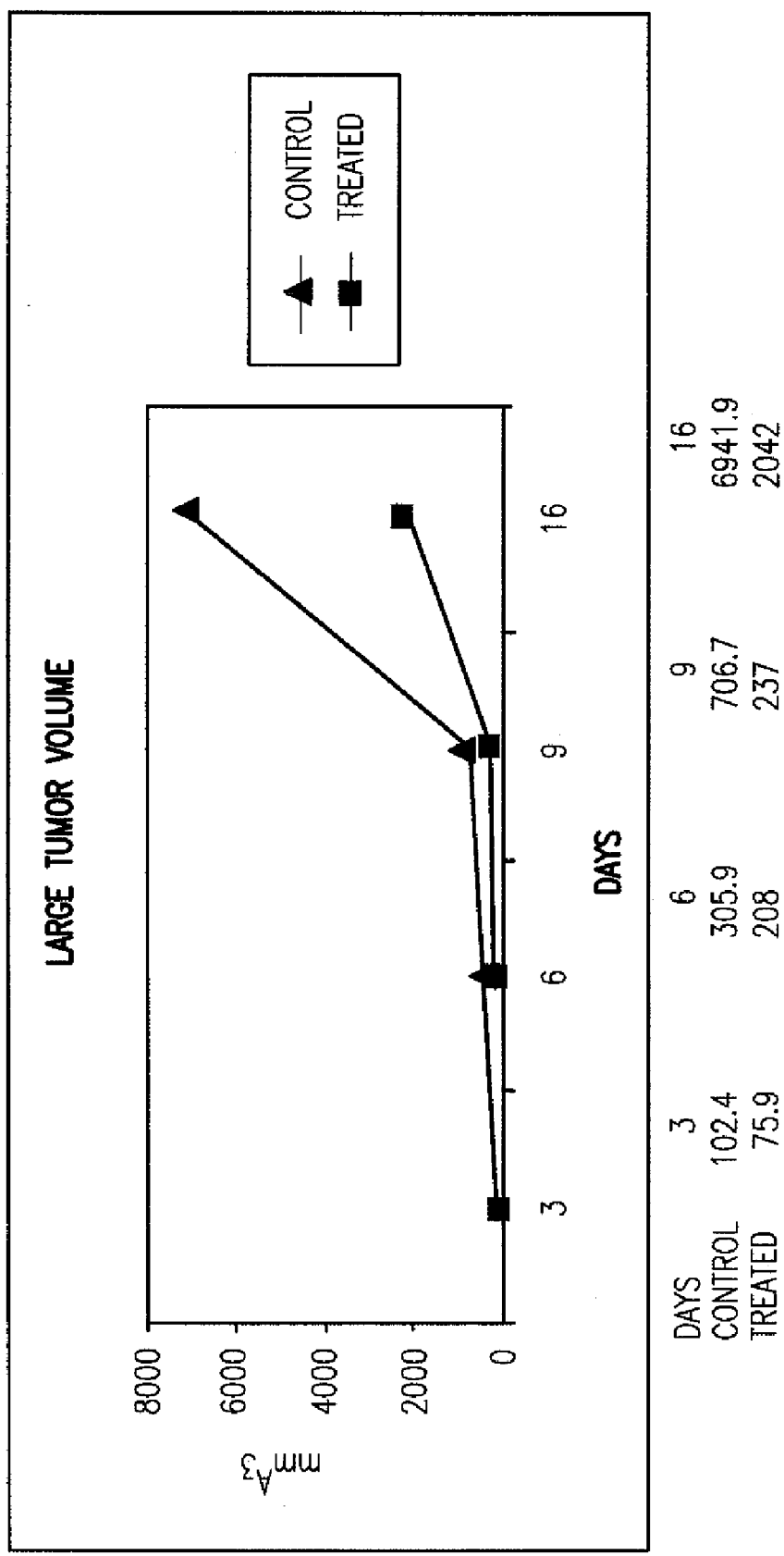

NATURAL LINIMENT FOR TREATMENT OF SKIN CANCERS

FIELD OF THE INVENTION

This invention comprises a liniment composed of natural substances which can be applied to skin cancer tumors to shrink the tumors or retard their growth.

BACKGROUND OF THE INVENTION

According to the American Cancer Society, each year there are thousands of new cases of skin cancers. The most serious type of skin cancer, melanoma, was estimated to have 62,190 cases in 2006, resulting in 7910 deaths, due to melanoma.

There are more than one million cases of non-melanoma (such as basal cell or squamous cell) skin cancer cases diagnosed yearly in the United States.

There have been compositions of natural substances suggested, such as the combination of powdered bloodroot, powdered ginger root and zinc chloride, for treatment of skin lesions, U.S. Pat. No. 4,515,779 issued to Elliott on May 7, 1985.

SUMMARY OF THE INVENTION

The liniment of this invention comprises primarily, pancreatin, pepsin, betaine HCL, emulsified vitamin A, and zinc. Also present are pancrelipase, fenugreek, papain, amylase and ox bile extract. The vitamin A is emulsified in water or in a mixture of water and acacia with d-alpha tocopherol as an anti oxidant.

The pancreatin, pepsin, betaine HCL, pancrelipase, fenugreek, papain, amylase and ox bile extract, can be obtained from various suppliers or can be obtained in a dietary supplement called Digest-All, manufactured by Immuno Screen of St. Petersburg, Fla.

The emulsified Vitamin A in a mixture of water and acacia, with d-alpha tocopherol as an anti oxidant, may be obtained in a dietary supplement called Bio-Ae-Mulsion Forte, manufactured by Biotics Research Corporation of Rosenberg, Tex.

The zinc may come in the form of zinc citrate.

There optionally may be added to the composition trace amounts of apple cider vinegar and minced garlic clove.

The liniment is prepared by grinding the ingredients in a mortar and pestle at ambient temperature where it reaches a thick salve consistency.

BRIEF DESCRIPTION OF THE DRAWINGS

FIG. 1 is a graph showing test treatments using the liniment of this invention.

DETAILED DESCRIPTION OF THE INVENTION

The amount of the ingredients in the liniment, by weight, are as follows:

| Ingredient | By weight |
| --- | --- |
| pancreatin | 10% to 20% |
| pepsin | 5% to 10% |
| betaine HCL | 15% to 30% |
| emulsified vitamin A | 5% to 15% |
| zinc citrate | 5% to 10% |
| pancrelipase | 10% to 20% |
| fenugreek | 10% to 20% |
| papain | 2% to 5% |
| amylase | 2% to 5% |
| ox bile extract | 5% to 15% |
| apple cider vinegar | optional trace amounts |
| garlic clove | optional trace amounts |

The basic ingredients may be present in approximately equal amounts.

Tests were conducted using the following liniment formula on human skin cancer grown in nude mice. In these tests, human cancer cells (fast growing) called Lox, were used. It took two weeks for the tumors to develop in the mice.

| Ingredient | By weight |
| --- | --- |
| pancreatin | 100 mg |
| pepsin | 50 mg |
| betaine HCL | 150 mg |
| emulsified vitamin A | 5 mg |
| zinc citrate | 50 mg |
| pancrelipase | 100 mg |
| fenugreek | 100 mg |
| papain | 25 mg |
| amylase | 40 mg |
| ox bile extract | 75 mg |
| apple cider vinegar | trace amount |
| garlic clove | trace amount |

The liniment was prepared by grinding the ingredients in a mortar and pestle at ambient temperature. The texture was that of a skin ointment, which was applied once daily to the tumors.

The tests were conducted on large, medium and small tumors. The graph of FIG. 1 shows results of treatment on large tumors. The tumor volume of a control group was compared to the tumor volume of a treated group. The results show that after 16 days of treatment the control group tumor volume increased from the third day to the sixteenth day by nearly 7000%, the treated group increased by only 2000%.

This proved that the liniment of this invention retarded the growth of the large tumors.

Separate test were conducted on small and medium sized tumors. The same formulation of the liniment was used. The table below compares the volume in cubic millimeters of the control group as compared to the treated group. In the small tumor treated group, several of the tumors completely disappeared.

Effect of Treatment on the Volume of Small and Medium Human Skin Cancer Tumors Grown in Nude Mice

| | Control (small) | | Treated (small) | | Control (medium) | | Treated (medium) | |
|---|---|---|---|---|---|---|---|---|
| | Mouse Number | Tumor Volume | Mouse Number | Tumor Volume | Mouse Number | Tumor Volume | Mouse Number | Tumor Volume |
| Dec. 17, 2006 | 1 | 23.95 | 1 | 22.4 | 1 | 68.62 | 1 | 61.74 |
| | 2 | 21.42 | 2 | 16.35 | 2 | 51.39 | 2 | 56.38 |
| | 3 | 16.17 | 3 | 16.13 | 3 | 47.95 | 3 | 51.44 |
| | 4 | 10.76 | 4 | 15.25 | 4 | 41.63 | 4 | 31.72 |
| | | | 5 | 14.75 | 5 | 28.33 | 5 | 29.79 |
| | | | 6 | 10.32 | | | | |
| Mean | | 18.075 | | 15.86666667 | | 47.584 | | 46.214 |
| Dec. 20, 2006 | 1 | 40.83 | 1 | 23.41 | 1 | 167.64 | 1 | 146.12 |
| | 2 | 27.46 | 2 | 0 | 2 | 99.71 | 2 | 124.16 |
| | 3 | 26.52 | 3 | 0 | 3 | 93.84 | 3 | 88.27 |
| | 4 | 22.44 | 4 | 0 | 4 | 80.5 | 4 | 85.44 |
| | | | 5 | 0 | 5 | 70.34 | 5 | 59.63 |
| | | | 6 | 0 | | | | |
| Mean | | 29.3125 | | 3.901666667 | | 102.406 | | 100.724 |
| % change of control | | | | 13.3 | | | | 98.36 |
| Dec. 23, 2006 | 1 | 87.85 | 1 | 57.89 | 1 | 285.93 | 5 | 282.44 |
| | 2 | 42.71 | 2 | 45.88 | 2 | 168.63 | 4 | 199.5 |
| | 3 | 29.8 | 3 | 28.19 | 3 | 168.27 | 2 | 161.42 |
| | 4 | 27.15 | 4 | 0 | 4 | 156.98 | 1 | 123.8 |
| | | | 5 | 0 | 5 | 141.79 | 3 | 66.33 |
| | | | 6 | 0 | | | | |
| Mean | | 46.8775 | | 21.99333333 | | 184.32 | | 166.698 |
| % change of control | | | | 46.9 | | | | 90.44 |

Having thus described the invention, I claim:

1. A method of reducing or limiting the growth of human melanoma skin cancer tumors comprising providing a liniment consisting of pancreatin, pepsin, betaine HCL, emulsified vitamin A, zinc, pancrelipase, fenugreek, papain, amylase ox bile extract, trace amounts of cider vinegar and trace amounts of minced garlic clove and applying the liniment to the tumors.

2. The method of reducing or limiting the growth of treating human skin cancer tumors of claim 1, wherein the application of the liniment is repeated a plurality of times.

3. The method of reducing or limiting the growth of treating human skin cancer tumors of claim 1, wherein the application of the liniment is repeated on a daily basis.

4. The method of reducing or limiting the growth of human skin cancer tumors of claim 1 in which the pancreatin, pepsin, betaine HCL, emulsified vitamin A, and zinc, pancrelipase, fenugreek, papain, amylase and ox bile extract ingredients are present in approximately equal amounts.

5. A method of reducing or limiting the growth of human melanoma skin cancer tumors comprising preparing a liniment consisting of pancreatin, pepsin, betaine HCL, emulsified vitamin A, zinc, pancrelipase, fenugreek, papain, amylase and ox bile extract and applying the liniment to the tumors.

6. The method of reducing or limiting the growth of human skin cancer tumors of claim 5 in which the ingredients are present in approximately equal amounts.

7. The method of reducing or limiting the growth of human skin cancer tumors of claim 5 in which the ingredients are ground together at ambient temperature until they reach a thick ointment consistency.

8. The method of reducing or limiting the growth of human skin cancer tumors of claim 5, wherein the application of the liniment is repeated a plurality of times.

9. The method of reducing or limiting the growth of treating human skin cancer tumors of claim 5, wherein the application of the liniment is repeated on a daily basis.

10. The method of reducing or limiting the growth of human skin cancer tumors of claim 1 or 5, wherein the vitamin A is emulsified in a solution selected from water and a mixture of water and acacia with d-alpha tocopherol as an antioxidant.

11. The method of reducing or limiting the growth of human skin cancer tumors of claim 1 or 5, wherein the zinc is in the form of zinc citrate.

* * * * *